United States Patent [19]
Rabin et al.

[11] Patent Number: 5,899,897
[45] Date of Patent: May 4, 1999

[54] METHOD AND APPARATUS FOR HEATING DURING CRYOSURGERY

[75] Inventors: Yoed Rabin; Thomas Benjamin Julian; Norman Wolmark, all of Pittsburgh, Pa.

[73] Assignee: Allegheny-Singer Research Institute, Pittsburgh, Pa.

[21] Appl. No.: 08/936,958

[22] Filed: Sep. 25, 1997

Related U.S. Application Data

[60] Provisional application No. 60/026,730, Sep. 26, 1996.

[51] Int. Cl.$^6$ ........................................... A61B 17/36
[52] U.S. Cl. .............................. 606/21; 606/27; 606/29
[58] Field of Search .......................... 606/20–26; 607/98, 607/113

[56] References Cited

U.S. PATENT DOCUMENTS

| | | |
|---|---|---|
| 3,910,277 | 10/1975 | Zimmer . |
| 4,719,919 | 1/1988 | Marchowsky et al. . |
| 4,947,842 | 8/1990 | Marchowsky et al. . |
| 4,989,601 | 2/1991 | Marchosky et al. . |
| 5,324,286 | 6/1994 | Fowle ........................................ 606/23 |

*Primary Examiner*—John P. Leubecker
*Assistant Examiner*—Roy Gibson
*Attorney, Agent, or Firm*—Ansel M. Schwartz

[57] ABSTRACT

The system includes a mechanism for freezing tissue in a patient. Additionally, the system includes a mechanism for heating other tissue near the tissue being frozen by the freezing mechanism such that essentially only desired region is frozen by the freezing mechanism and heat from the heating mechanism prevents the other tissue from being frozen. The heating mechanism is disposed adjacent to but separate and apart from the freezing mechanism. Alternatively, the mechanism for heating can be used with tissue already frozen by the freezing mechanism. A method for performing cryosurgery on a patient. The method includes the steps of inserting a cryoprobe into a patient. Next, there is the step of placing a cryoheater in contact with the patient adjacent the cryoprobe. Then, there is the step of activating the cryoprobe and the cryoheater so the cryoprobe freezes desired tissue in the patient and the cryoheater heats other tissue around the desired tissue so the other tissue is not frozen by the cryoprobe. Alternatively, there can be the step of activating the cryoheater after the cryoprobe has frozen the desired tissue to thaw the frozen tissue.

6 Claims, 3 Drawing Sheets

METHOD AND APPARATUS FOR HEATING DURING CRYOSURGERY

This application claims the benefit of U.S. Provisional application No.: 60/026,730, filed Sep. 26, 1996.

FIELD OF THE INVENTION

The present invention relates generally to cryosurgical devices and procedures. More particularly, the invention concerns a cryosurgical apparatus that has the abilities to either control the thawing stage of a cryosurgical procedure; prevent the freezing front from propagation into undesired directions; or, protect tissues from freezing within the cryotreated region or nearby. The mainstay of the new invention is a temperature controlled electrical heater which will be termed cryoheater from hereon.

BACKGROUND OF THE INVENTION

Cryosurgery, or the destruction of undesired biological tissues by freezing, has long been accepted as an important alternative technique of surgery (Orpwood, 1981; Rubinsky and Onik, 1991; Gage, 1992). Compared with conventional means of destroying tissues, such as surgical excision, radiotherapy and immunotherapy, visceral cryosurgery (especially minimally invasive cryosurgery) offers the following potential advantages: simplicity of the procedure, minimal bleeding, anaesthetic effect of low temperatures, short period of patient recovery, low cost, minimal scarring, and possible stimulation of the body's immune system.

James Arnott, an English physician, was the first to introduce the technique of destruction of biological tissues by freezing in 1865. Since Arnott's first report, numerous cryodevices and techniques have been suggested. These have included pre-cooled metal blocks, spray/pour freezing with liquefied gases, refrigeration systems, thermoelectric methods, dry ice applications, cryogenic heat pipes, Joule-Thompson effect based cryoprobes and boiling effect based cryoprobes. However, as a result of the high cooling power usually needed for cryosurgery, and especially of internal organs, the boiling effect and the Joule-Thompson effect have been found to be the preferable cooling technique by most cryosurgeons.

Cryosurgical success, or maximal destruction of undesired biological tissues by freezing, is influenced by many factors: the cooling rate (Smith and Fraser, 1974; Gage, 1985; Fahy, 1990), the thawing rate (Miller and Mazur, 1976), the minimal temperature achieved (Gage, 1982), and the number of repeated freezing/thawing cycles (Rand et al., 1985). Many controlled cryodevices and cryoprotocols have been suggested to improve the cryodestruction, where the controlled variable is the cryoprobe temperature. Additional thermocouples, which are distributed in the cryotreated region, are used in some cases as an external feedback for the control system. In some other cases the electrical impedance of the cryotreated tissue is used as an additional indicator of cryodestruction. Most suggested cryoprotocols deal with the cooling stage of the cryoprocedure and therefore extensive efforts have been made to develop cryoprobes that can be accurately controlled within this stage. Some cryoprobes have a further ability of controlled heating at the thawing stage of the cryoprocedure (Fillipi, 1971; Merry and Smidebush, 1990; Rabin et al., 1995). The controlled thawing process is performed either by forcing hot working fluids through the cryoprobe's passageways or by activation of an electrical heater which is an integral part of the cryoprobe.

Cryosurgery of internal organs, and especially minimally invasive cryosurgery, is monitored by one of the following imaging techniques: ultrasound, CT or NMR. However, ultrasound is the most accepted imaging technique among cryosurgeons. Utilizing these techniques, the cryosurgeon inserts the cryoprobe(s) into the expected cryotreated region. Then, the cryosurgeon activates the cryoprobe according to some cooling protocol and monitors the frozen region growth (which is also termed "ice-ball"). When the undesired tissues are completely frozen, or when there is a danger of cryodestruction to important surrounding tissues, the cryosurgeon terminates the cooling process and the thawing stage follows. In some cases the cooling\thawing stages are repeated in order to increase the cryodestruction.

SUMMARY OF THE INVENTION

It is an objective of the invention to provide a method and apparatus to reduce the duration of a single-cycle or multi-cycle cryoprocedure. More particularly, it is the objective of the invention to provide a method and apparatus for heating in order to minimize the thawing stage duration of the cryoprocedure.

Another objective of the invention is to provide a method and apparatus to control the shape of the ice ball and to prevent the freezing from propagation into undesired direction, in order to reduce or to eliminate cryodestruction of surrounding tissues.

Yet another objective of the invention is to provide a method and apparatus for prevention of tissues freezing within the ice-ball region.

A further objective of the invention is to provide a method and apparatus for increasing of cryodestruction by means of control of the thawing rate.

The present invention pertains to a cryoheater for insertion into a patient. The cryoheater comprises a shell. The cryoheater also comprises a heating mechanism within the shell. Preferably, the cryoheater includes a sensor which determines the temperature of the shell. The sensor is adjacent to the shell.

The present invention pertains to a system for performing cryosurgery on a patient. The system comprises a mechanism for freezing tissue in a patient. Additionally, the system comprises a mechanism for heating other tissue near the tissue being frozen by the freezing mechanism such that essentially only desired pressure is frozen by the freezing mechanism and heat from the heating mechanism prevents the other tissue from being frozen. The heating mechanism is disposed adjacent the freezing mechanism.

The present invention pertains to a system for performing cryosurgery on a patient. The system comprises a mechanism for freezing tissue in a patient. Also, the system comprises a mechanism for heating the tissue frozen by the freezing mechanism. The heating mechanism is disposed adjacent the freezing mechanism.

The present invention pertains to a method for performing cryosurgery on a patient. The method comprises the steps of inserting a cryoprobe into a patient. Next, there is the step of inserting a cryoheater into a patient adjacent the cryoprobe. Then, there is the step of activating the cryoprobe and the cryoheater so the cryoprobe freezes desired tissue in the patient and the cryoheater heats other tissue around the desired tissue so the other tissue is not frozen by the cryoprobe.

The present invention pertains to a method for performing cryosurgery on a patient. The method comprises the steps of inserting a cryoprobe into a patient. Then, there is the step of inserting a cryoheater into a patient adjacent the cryoprobe. Next, there is the step of activating the cryoprobe so the cryoprobe freezes desired tissue in the patient. Then, there is the step of activating the cryoheater after the cryoprobe has frozen the desired tissue to heat the frozen tissue.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
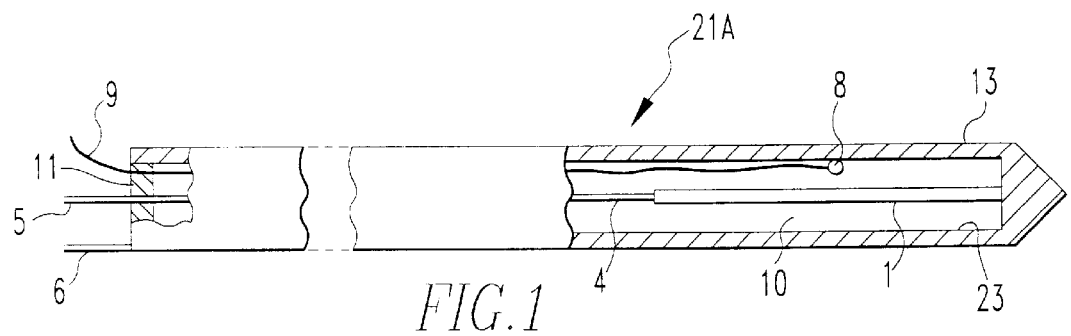
FIG. 1 is a side view of cryoheater 21A.

Referring now to the drawings wherein like reference numerals refer to similar or identical parts throughout the several views, and more specifically to FIGS. 1–4 thereof, there is shown three forms of cryoheaters for insertion into a patient (FIGS. 1–3) and one form of a ntrol mechanism (FIG. 4) are thereshown. The cryoheater 21 comprises a shell 13. The cryoheater 21 also comprises a heating mechanism 23 within the shell 13. Preferably, the cryoheater 21 includes a sensor 8 which determines the temperature of the shell 13. The sensor 8 is adjacent to the shell 13.

Preferably, the heating mechanism 23 includes an electrical resistor 1 disposed in the shell 13. The heating mechanism 23 preferably includes a control mechanism 24 which provides a desired electrical power, such as current, to the resistor 1. Preferably, the control mechanism 24 includes a controller 25 which controls the amount of electrical power provided to the resistor 1. Additionally, the heating mechanism 23 includes a "+" terminal in connection with the electrical resistor 1 and a "−" terminal in connection with the electrical resistor 1 so electrical current flows only in or through the shell 13 but not in a patient. The heating mechanism 23 preferably also includes electrical isolator material disposed in the shell 13 between the resistor 1 and the shell 13.

The controller 25 preferably controls the temperature of the shell 13 by controlling the amount of electrical power provided to the electrical resistor 1 in accordance with the desired temperature forcing function. Preferably, the control mechanism 24 includes a temperature unit 27 connected to the sensor 8 for reading temperature signals from the sensor 8 and producing a temperature control signal. A controller 25 provides electrical power to the electrical resistor 1 corresponding to the difference between the forcing function and the temperature control signal.

Preferably, the shell 13 has a tip which is pointed. In one embodiment the shell 13 is made of metal and has a connector extending from an end opposite the tip. The connector is the "−" terminal. The electrical resistor 1 in this embodiment is connected to the tip so electrical current flows through the resistor 1, along the shell 13 and to the connector. Alternatively, the electrical resistor 1 has a first connector which is the "+" terminal and a second connector which is a "−" terminal and the resistor 1 forms a loop which is disposed in the shell 13. In another alternative embodiment, the shell 13 is made of metal, and has a rounded tip. The heating mechanism 23 in this embodiment includes a flexible tube connected to the shell 13 and a flexible electrical conductor 15 disposed in the flexible tube in which electrical current carrying wires are disposed and connected to the resistor 1. The flexible electrical conductor 15 is directly connected to the shell 13.

The present invention pertains to a system 30 for performing cryosurgery on a patient. The system 30 comprises a mechanism 32 for freezing tissue in a patient. Additionally, the system 30 comprises a mechanism 23 for heating other tissue near the tissue being frozen by the freezing mechanism 32 such that essentially only desired pressure is frozen by the freezing mechanism 32 and heat from the heating mechanism 23 prevents the other tissue from being frozen. The heating mechanism 23 is disposed adjacent the freezing mechanism 32.

The present invention pertains to a system 30 for performing cryosurgery on a patient, as shown in FIGS. 5a–5f. The system 30 comprises a mechanism 32 for freezing tissue, such as cryoprobe 22, in a patient. Also, the system 30 comprises a mechanism 23 for heating the tissue frozen by the freezing mechanism 32. The heating mechanism 23 is disposed adjacent the freezing mechanism 32. The heating mechanism 23 can be a cryoheater 21.

The present invention pertains to a method for performing cryosurgery on a patient. The method comprises the steps of inserting a cryoprobe 22 into a patient. Next, there is the step of inserting a cryoheater 21 into a patient adjacent the cryoprobe 22. Then, there is the step of activating the cryoprobe 22 and the cryoheater 21 so the cryoprobe 22 freezes desired tissue in the patient and the cryoheater 21 heats other tissue around the desired tissue so the other tissue is not frozen by the cryoprobe 22.

The present invention pertains to a method for performing cryosurgery on a patient. The method comprises the steps of inserting a cryoprobe 22 into a patient. Then, there is the step of inserting a cryoheater 21 into a patient adjacent the cryoprobe 22. Next, there is the step of activating the cryoprobe 22 so the cryoprobe 22 freezes desired tissue in the patient. Then, there is the step of activating the cryoheater 21 after the cryoprobe 22 has frozen the desired tissue to heat the frozen tissue.

In the operation of the invention, cryoheater 21A, FIG. 1, is comprised of a metallic cryoheater shell 13, which has a tube configuration and a sharp pointed tip, for penetration into either the cryotreated tissues or the surrounding tissues. Electrical resistor 1 is connected to the tube's tip through the tube's hollow center. Current carrying wire 4 is connected to the other end of electrical resistor 1, on its one end, and is connected to electrical connector 5, on its other end. Electrical connector 6 is a metallic extension of cryoheater shell 13. On the inner surface of cryoheater shell 13, and near the center of electrical resistor 1, temperature sensor 8 is attached. Temperature sensor wires 9 transfer signals from temperature sensor 8 to the control system. The gap between tube 13, electrical resistor 1 and current carrying wire 4, is filled with an electrical isolator material. The electrical isolator material within cryoheater shell 13 is sealed with cover 11.

The heating process of cryoheater A takes place as follows. Electrical power is supplied to the cryoheater through electrical connectors 5 and 6. The electrical power is transferred through current carrying wire 4 and cryoheater shell 13, respectively, to both ends of electrical resistor 1, which serves as a heating element. Connector 6 is connected to the "0" pole of the electric circuit, while connector 5 is connected to the "+" pole of the power source for safety reasons. Therefore, in case of electrical circuit failure no current will be transferred through the tissues to the ground.

The cryoheater should be controlled by a controller to maintain a constant and pre-specified temperature. The temperature control process of the cryoheater is presented schematically in FIG. 4 and is described hereon. The temperature of the cryoheater surface is sensed by temperature sensor 8, FIG. 1. The signals are transferred through temperature sensor wires 9, FIG. 1. The signals are amplified and read by a temperature unit, and then are converted into signals which are compatible with the controller's input, FIG. 4. The controller output is proportional to the difference between a desired temperature forcing function and the measured cryoheater temperature. The "forcing function" is the desired temperature of the cryoheater outer surface (this term is taken from the Theory of Control and is a well known term). Moreover, the temperature forcing function is the temperature function that the operator "asks" the controller to force the system. The desired forcing function is designated by r in FIG. 4. This function is forced as follows: the cryoheater's surface temperature is measured by the temperature sensor 8 via the temperature unit, FIG. 4; the controller compares the desired forcing function, r, and the value read by the temperature unit and applied the control law; if the cryoheater temperature is lower than the desired temperature, the control law will sign the controller to activate the power amplifier, however if the cryoheater temperature is higher than the desired temperature, the control law will sign a zero output. It follows that the forcing function is an arbitrary function that the operator would like to force the system, the control unit does the job using temperature measurements as a feedback. The control law can be formulated in many ways as is well established in the Theory of Process Control. For the application of cryoheaters it seems that even the simplest, on-off controller should be satisfactory.

The controller output is amplified to obtain a desired heating power in the cryoheater. The electric power is transferred from the power amplifier to electrical resistor 1 through connectors 5 and 6 of the cryoheater, FIG. 1. It is preferred (but not necessary) to materialize the control unit by a microcomputer, which can very easily control many cryoheaters simultaneously.

Figure 4:
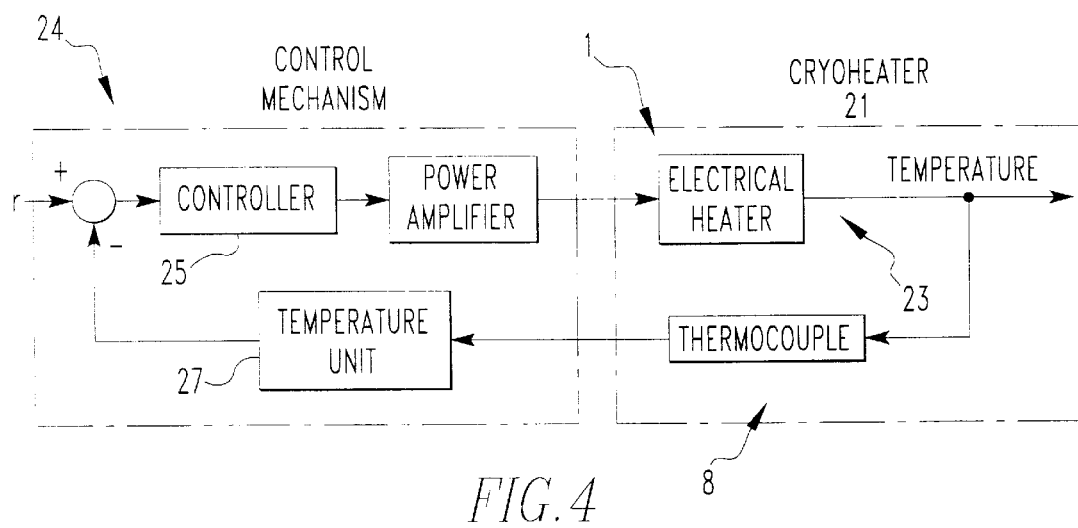
FIG. 4 is a generally schematic view illustrating one form of control mechanism of the cryoheater of the invention.

There are many alternative techniques to materialize the control unit presented by FIG. 4 of which two will be discussed here. The control unit can be assembled from off-the-shelf components. As an example, and only as an example, off-the-shelf Omega® temperature amplifiers, controllers, and switching devices can be assembled to create the control unit (Omega, The Temperature Handbook™, Vol. 29, 1995).

Alternatively, the control unit can be microcomputer based, with a similar temperature unit and a power amplifier used for controlling the temperature of an electrical heated cryoprobe, as is described in detail by Rabin and Shitzer ("A New Cryosurgical Device for Controlled Freezing, Part I: Setup and Validation Test, *Cryobiology*, Vol. 33, pp. 82–92, 1996, incorporated by reference herein).

The temperature unit is an integral part of some of the commercial control units (there). In general, the control unit and the temperature units are very standard components in process control and I am not sure we have to write too much about them. If one should like to learn about the design criteria of such a control unit he should read my above reference.

Figure 2:
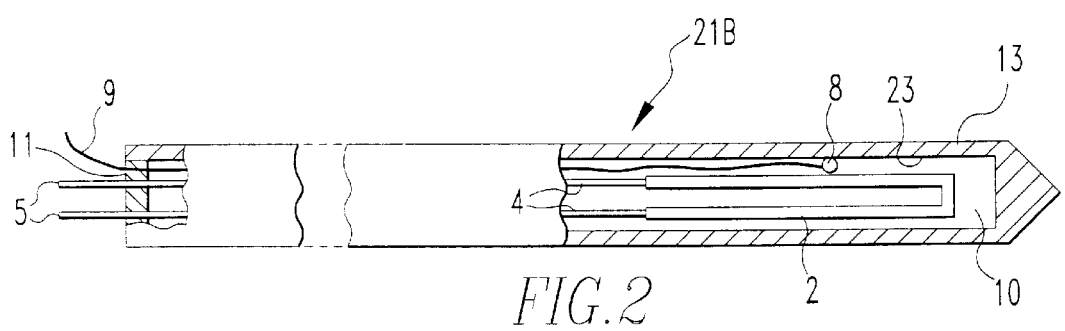
FIG. 2 is a side view of cryoheater 21B.

Cryoheater 21B, FIG. 2, is similar to cryoheater A with the only exception that tube 13 is electrically isolated from the electrical circuit. Therefore, cryoheater shell 13 can be made of non-metallic materials in this case. Electrical resistor 2 has a U shape. Two identical current carrying wires 4 are connected to both electrical resistor 2 ends, and two identical electrical connectors 5 are connected to the other ends, respectively. The control loop and the heating process, which dominates and activates cryoheater B, respectively, are identical to those described above for cryoheater A.

Figure 3:
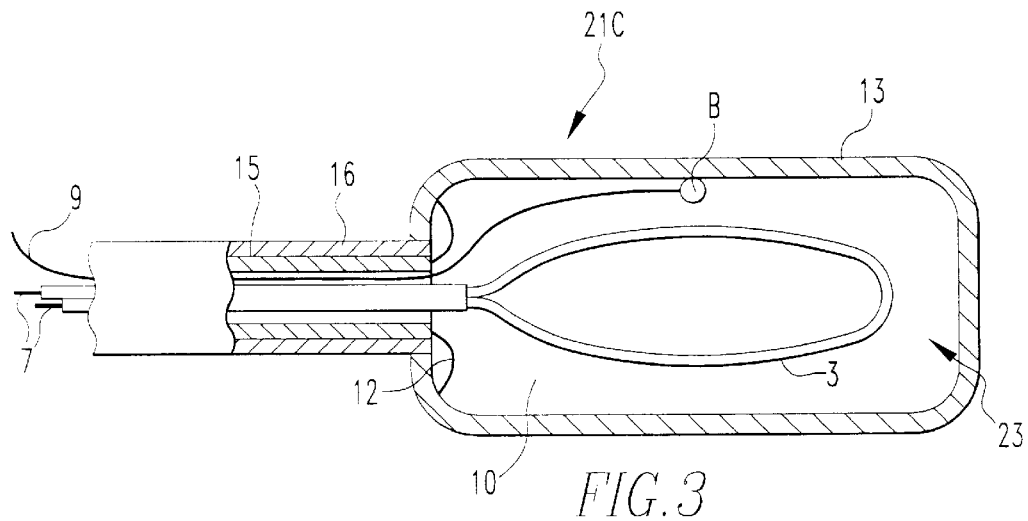
FIG. 3 is a side view of cryoheater 21C.

Cryoheater 21C, FIG. 3, comprised of a metallic cryoheater shell 13 has a rounded or half a spherical tip for its insertion through blood vessels, urethra, or other anatomical passageways. Leading tube 16 is flexible and is connected onto cryoheater shell 13 and carries all current carrying wires. A hollow and flexible electrical conductor 15 is placed inside tube 16, and carries all the rest of current carrying wires. Electrical conductors 12 connect flexible conductor 15 to metallic tube 13. Electrical resistor 3 is located inside cryoheater shell 13 and is powered through the current carrying wires 7. Temperature sensor 8 is attached to the inner surface of cryoheater shell 13. The temperature sensor signals are transferred through temperature sensors wires 9, which are located inside cryoheater shell 13 and thereafter inside flexible conductor 15. The gap between electrical resistor 3 and cryoheater shell 13 is filled with an electrical isolator material. For safety reasons, electrical conductor 15 is grounded at all times. Cryoheater shell 13 and conductor 15 and connectors 12 serve as a grounded shell for the electrical circuit for safety reasons.

The heating process and the control process of cryoheater C are very similar to those of cryoheaters A and B. The internal structure of cryoheater C, however, is different. The main reason for this difference is that cryoheater C has to have the ability to be inserted through curved anatomical passageways. Therefore, only the active part of cryoheater C is rigid, while the leading tube and its internal electrical conductors are flexible.

As a surgical tool, the cryoheater shell should be made of stainless steel. The diameter of the cryoheater can be reduced down to an 18-gage needle size. The power supply can be either electrical batteries or 110V/12V convertor, which in both cases are designed for high power. From heat transfer consideration the cryoheater should have a power of at least 12 W.

Before commencing the cryosurgery, the cryosurgeon will typically study the location, depth and configuration of the undesired tissues. The cryosurgeon will evaluate the surrounding healthy tissues as well, and especially the vital tissues. This evaluation can be performed via ultrasound, CT or NMR imaging techniques. Based on this study, one or more appropriately configured cryoprobes, in combination of one or more appropriately configured cryoheaters, will be chosen. In general, cryoheaters can be used in one of two modes: thawing or freezing prevention.

The thawing mode is addressed first. Based on a thorough study as presented above, one or more appropriately configured cryoprobes will be chosen. The frozen region size and configuration will be estimated. Based on the expected frozen region size and configuration, one or more appropriately configured cryoheaters will be chosen to perform thawing as efficiently as possible. The cryoprobe(s) and the cryoheater(s) will be placed in the cryotreated region at the very beginning of the procedure, prior of any cryoprobe activation. The freezing stage will then be started. The cryoprobe(s) will be operated, according to a cooling protocol to ensure maximal cryodestruction, until a complete freezing of the desired region is achieved. The thawing stage will then be started. The cryoheater(s) will be controlled to ensure complete thawing. Some cryoprobes have a capability of heating which can be used in combination with the cryoheaters. The freezing/thawing cycle will be repeated in case of multi-cycle cryosurgery.

Examples of cryoprobe(s) and cryoheaters configurations for thawing mode are presented in FIG. 5: (a) single cryoprobe for superficial cryotreatment in combination with cryoheaters (side view); (b) single cryoprobe for invasive cryotreatment in combination with cryoheaters (side view); (c) triple-cryoprobe cryotreatment in combination with 7 cryoheaters (viewed in a direction parallel to the cryoprobes' center lines). Cryoprobes A or B, FIGS. 1 and 2, respectively, will typically be used for the above cases.

The cryoheater's temperature is the controlled variable of the apparatus. The controller forcing function can be a step function to reduce thawing duration to minimum, on the one hand, but to prevent over heated tissues, on the other hand. The temperature of the step can be carefully chosen as the normal body temperature or higher. It is noted that hyperthermia damage due to cryoheaters' over heating can increase the tissues' destruction, but yet needs to be carefully done. An alternative forcing function is resulted from the dependency of the cryodestruction in the thawing rate. This alternative forcing function is resulted from an inverse mathematical problem in which its solution gives a constant thawing rate at the thawing front. However, the utilization of the alternative forcing function requires further scientific study.

The method for freezing prevention is addressed next. In general, freezing prevention can take place either at the edge of the freezing region or in some tissues which are surrounded by other freezing tissues. Based on the preoperative study presented above, one or more appropriately configured cryoprobes will be chosen. The frozen region size and configuration will be estimated. One or more appropriately configured cryoheaters will be chosen, in order to prevent freezing propagation into undesired direction, or in order to prevent freezing of some tissues which will be surrounded by frozen tissues. The cryoprobe(s) and the cryoheater(s) will be placed in the cryotreated region at the very beginning of the procedure, prior of any cryoprobe activation. The cryoheater(s) will be activated and set to the range of the undisturbed tissues' temperature. These cryoheaters will be operated all along the cryoprocedure, until complete thawing has been achieved. The freezing stage will then be started. The cryoprobe(s) will be operated, according to a cooling protocol to ensure maximal cryodestruction, until a complete freezing of the target region is achieved. The thawing stage will then take place. The freezing\thawing cycle will be repeated in case of multi-cycle cryosurgery.

Examples of cryoprobe(s) and cryoheater(s) configurations for the freezing prevention mode are presented in FIG. 5: (d) preventing the freezing process from propagation into undesired direction, which in this case is perpendicular to the cryoheaters line (viewed in a direction parallel to the cryoprobe's center lines); (e) protecting blood vessel from freezing (side view); (f) protecting the urethra during cryosurgery of the prostate (viewed in a direction parallel to the cryoprobes' center lines).

The cryoprobes will be inserted into the prostate in the same common techniques already used today. The present invention does not deal with the cryoprobes insertion. The cryoheater will be inserted through the urethrae similar to the insertion of a catheter. The tube 16 and the electrical conductor 15 are flexible in this case.

The cryoheaters are placed at the end of long rigid tubes made from the same material as needles. The cryoheater insertion is a minimal invasive procedure since its insertion is similar to the insertion of long needles. The cryoheater's diameter can vary between 1 mm to a few millimeters, depending on the application.

Figure 5A:
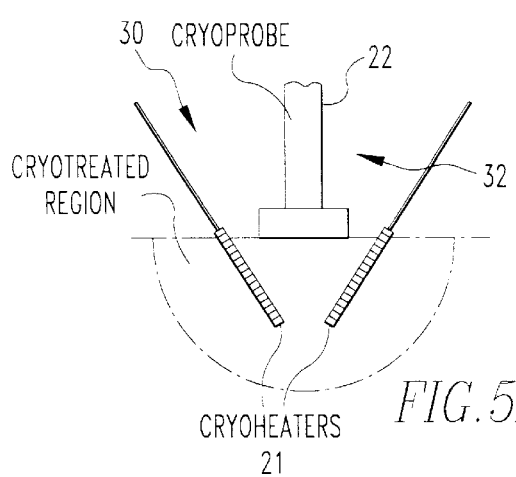
FIG. 5 is diagrammatic representation showing examples of cryoprobe(s) and cryoheater(s) configurations for different operations: (a) single cryoprobe for superficial cryotreatment in combination with cryoheaters (side view); (b) single cryoprobe for invasive cryotreatment in combination with cryoheaters (side view); (c) triple-cryoprobe cryotreatment in combination with 7 cryoheaters (viewed in a direction parallel to the cryoprobes' center lines); (d) preventing the freezing process from propagation into undesired direction, which in this case is perpendicular to the cryoheaters line (viewed in a direction parallel to the cryoprobe's center lines); (e) protecting blood vessel from freezing (side view); (f) protecting the urethra during cryosurgery of the prostate (viewed in a direction parallel to the cryoprobes' center lines).
Figure 5B:
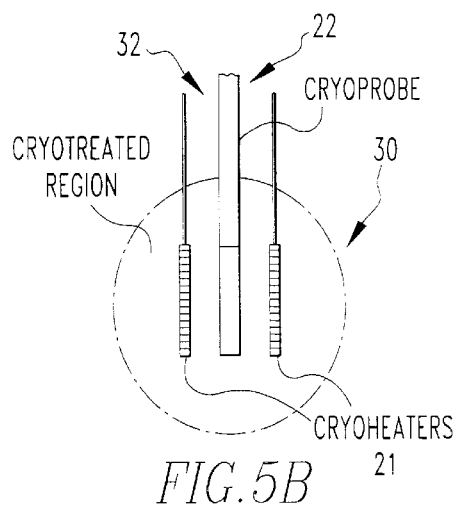
Figure 5C:
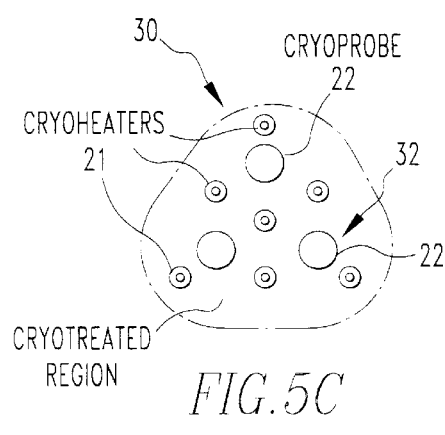
Figure 5D:
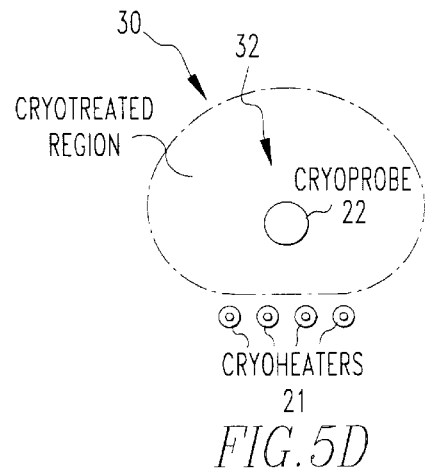

With regard to the distribution of a plurality of cryoheaters:

1. The cryoheaters should be equally distributed in space for the application of controlled thawing in cryotreated tissue, as shown in FIGS. 5a, 5b and 5c.

Figure 5E:
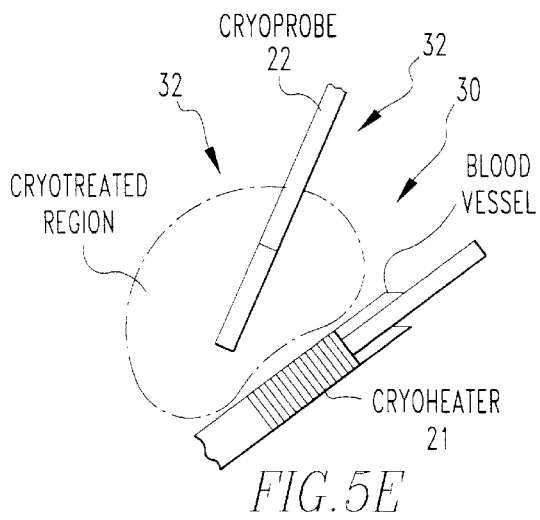
Figure 5F:
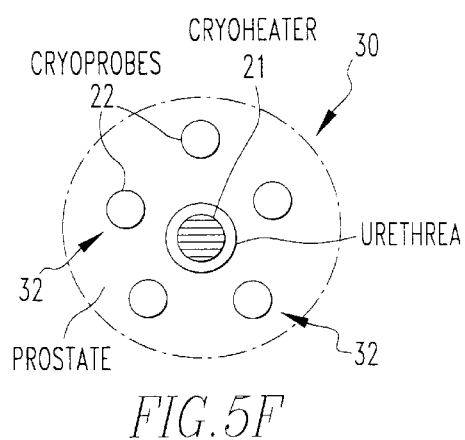

2. The cryoheater should be placed as close as possible to the cryoprobe, within the protected vessel, in case of freezing prevention of blood vessels, urethrae, or other anatomical passageways, as shown in FIGS. 5e and 5f.

The destruction of the undesired tissues (cryotreated tissues) is done by freezing the tissues, therefore the cryoprobes are the main surgical tools. The cryoheaters are used to reduce the duration of the cryoprocedure and to save vital organs or tissues in adjunct to the cryotreated tissues, and to assist in shaping the frozen region.

Two modes for the cryoheaters application have been presented here, for thawing and for freezing prevention, respectively. However, cryoheaters operating under these two modes can be combined to provide freezing prevention of some tissues and controlled thawing of other tissues in the same cryoprocedure.

A cryoheater having a similar configuration to the one presented in FIG. 2, cryoheater B has, for example, the following design. Cryoheater shell 13 was made of a copper tube having a diameter of 2.4 mm OD (1.7 mm ID) and a length of 0.50 mm. One end of the tube was soldered and machined into a sharp pointed tip configuration, in an angle of 35°.

The electrical heating element was constructed as follows. A 22-gage current carrying wire (0.7 mm OD), coated by a plastic insulation having a diameter of 1.2 mm, was used as the core of the electrical heater. The length of the wire was cut to fit into the hollow of the cryoheater shell. A standard electrical resistor wire, having a resistance of 12 $\Omega$ and a length of 100 mm, was taken out from a power resistor that was rated 20 W. The electrical resistor was carefully coiled around the plastic insulation of the current carrying wire, in such a way that no contact was made between one coil ring to another. The electrical resistor covered a total length of 20 mm starting at one end of the current carrying wire. One end of the electrical resistor was connected to the adjunct end of the current carrying wire, while the other end was lead along the plastic insulation, toward the other current carrying wire end. The coiled electrical resistor was coated with glue (Clear Epoxy), to fix its position and to provide a complete electrical insulation for the electrical resistor wire. The outer diameter of the glue was less than the ID of the cryoheater shell, i.e. 1.7 mm.

After the glue dried, the assembly of the current carrying wire and the electrical resistor was inserted into the cryoheater shell, leaving both ends of the current carrying wire and of the electrical resistor outside of the cryoheater shell. The electrical heater was connected in series with an on/off switch onto an electrical power source of 12 V and 1 Amp. The electrical power source was a simple AC/DC convertor from the 110V electrical network. While the electrical heater is "on" it can give a power of up to 12 W.

A copper-constantan thermocouple was connected to the cryoheater shell, about 10 mm from its sharp pointed tip. Alternatively to what was presented above, the thermocouple was connected onto the cryoheater shell outer surface. This connection has no affect on the results.

The cryoheater was inserted in water as a substitute for the biological tissues. The cryoheater was placed at the center of a water container having a diameter of 17 cm and a depth of 6.5 cm. The cryoheater tip was immersed into a depth of 4 cm from the water level and was held with a supporting device. The water container, together with the supporting device and the cryoheater were placed in a freezer (−20° C.) for about 24 hours, until all of the water was frozen. After a complete freezing, the container with the cryoheater were taken out from the freezer and the cryoheater was connected to the electrical circuit and activated.

The temperature of the cryoheater outer surface was elevated from about −20° C. up to 65° C. within about 20 seconds. The ice, which was in contact with the outer surface of the cryoheater, started to melt almost immediately. An unfrozen region (thawed ice) developed around the cryoheater, having a larger diameter near the cryoheater tip and narrower diameter near the ice surface. The diameter of melted ice near the ice surface reached 8 mm within 70 sec of activation of the cryoheater.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A cryoheater for insertion into a patient comprising:
   a shell, the shell has a tip which is pointed;
   a heating mechanism within the shell, the heating mechanism includes an electrical resistor disposed in the shell, the heating mechanism includes a control mechanism which provides a desired electrical power to the electrical resistor, the control mechanism includes a controller which controls the amount of electrical power provided to the electrical resistor, the heating mechanism includes a "+" terminal in connection with the electrical resistor and a "−" terminal in connection with the electrical resistor so electrical current flows only in or through the shell but not in the patient, the heating mechanism includes electrical insulation material disposed in the shell between the electrical resistor and the shell, the controller controls the temperature of the shell by controlling the amount of electrical power provided to the electrical resistor in accordance with a desired temperature forcing function which defines the temperature of the shell over time, the control mechanism includes a temperature unit connected to the sensor for reading temperature signals from the sensor and producing a temperature control signal, said controller providing electrical power to the electrical resistor corresponding to the difference between said forcing function and the temperature control signal; wherein the shell is made of electrically conductive material and has a connector extending from an end opposite the tip, said connector being the "−" terminal; and wherein the electrical resistor is connected to the tip so electrical current flows through the resistor, along the shell and to the connector;
   a sensor which determines the temperature of the shell, said sensor adjacent to said shell.

2. A system for performing cryosurgery on a patient comprising:
   a mechanism for freezing tissue in a patient; and
   a mechanism for heating other tissue near the tissue being frozen by the freezing mechanism such that essentially only desired tissue is frozen by the freezing mechanism and heat from the heating mechanism prevents the other tissue from being frozen, said heating mechanism disposed adjacent to but physically separate and distinct from the freezing mechanism.

3. A method for performing cryosurgery on a patient comprising the steps of:
   inserting a cryoprobe into a patient;
   inserting a cryoheater into a patient adjacent the cryoprobe; and
   activating the cryoprobe and the cryoheater so the cryoprobe freezes desired tissue in the patient and the cryoheater heats other tissue around the desired tissue so the other tissue is not frozen by the cryoprobe.

4. A system for performing cryosurgery on a patient comprising:
   a mechanism for freezing tissue in a patient; and
   a mechanism for heating the tissue frozen by the freezing mechanism, said heating mechanism disposed adjacent to but physically separate and distinct from the freezing mechanism.

5. A method for performing cryosurgery on a patient comprising the steps of:
   inserting a cryoprobe into a patient;
   inserting a cryoheater into a patient adjacent the cryoprobe; and
   activating the cryoprobe so the cryoprobe freezes desired tissue in the patient; and
   activating the cryoheater after the cryoprobe has frozen the desired tissue to heat the frozen tissue.

6. A cryoheater for insertion into a patient comprising:
   a shell, the shell has a tip which is pointed;
   a heating mechanism within the shell, the heating mechanism includes an electrical resistor disposed in the shell, the heating mechanism includes a control mechanism which provides a desired electrical power to the electrical resistor, the control mechanism includes a controller which controls the amount of electrical power provided to the electrical resistor, the heating mechanism includes a "+" terminal in connection with the electrical resistor and a "0" terminal in connection with the electrical resistor so electrical current flows only in or through the shell but not in the patient, the heating mechanism includes electrical insulation material disposed in the shell between the electrical resistor and the shell, the controller controls the temperature of the shell by controlling the amount of electrical power provided to the electrical resistor in accordance with a desired temperature forcing function which defines the temperature of the shell over time, the control mechanism includes a temperature unit connected to the sensor for reading temperature signals from the sensor and producing a temperature control signal, said controller providing electrical power to the electrical resistor corresponding to the difference between said forcing function and the temperature control signal, the shell is made of electrically conductive material, and has a rounded tip, and wherein the heating mechanism includes a flexible tube connected to the shell and a flexible electrical conductor disposed in the flexible tube in which electrical current carrying wires are disposed and connected to the resistor, said flexible electrical conductor directly connected to the shell, at one end and electrically grounded at the other end; and a sensor which determines the temperature of the shell, said sensor adjacent to said shell.

* * * * *